US00PP15843P2

(12) United States Plant Patent
Dümmen

(10) Patent No.: US PP15,843 P2
(45) Date of Patent: Jul. 5, 2005

(54) ***POINSETTIA* PLANT NAMED 'DUEJOKER'**

(50) Latin Name: *Euphorbia pulcherrima*
Varietal Denomination: Duejoker

(75) Inventor: Marga Dümmen, Rheinberg (DE)

(73) Assignee: Dümmen Jungpflanzen Gbr, Rheinberg (DE)

( * ) Notice: Subject to any disclaimer, the term of this patent is extended or adjusted under 35 U.S.C. 154(b) by 0 days.

(21) Appl. No.: 10/859,522

(22) Filed: Jun. 1, 2004

(51) Int. Cl.[7] ..... A01H 5/00
(52) U.S. Cl. ..... Plt./303
(58) Field of Search ..... Plt./303

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Poinsettia* plant named 'Duejoker', characterized by its inflorescences with inflorescences with red and yellow bi-colored flower bracts; dark green-colored leaves; uniform and rounded plant habit; early flowering; large and showy cyathia; and excellent post-production longevity.

1 Drawing Sheet

Botanical classification/cultivar denomination: *Euphorbia pulcherrima* Willd. cultivar Duejoker.

BACKGROUND OF THE INVENTION

The present Invention relates to a new and distinct cultivar of *Poinsettia* plant, botanically known as *Euphorbia pulcherrima* Willd., and hereinafter referred to by the name 'Duejoker'.

The new *Poinsettia* is a product of a planned breeding program conducted by the Inventor in Rheinberg, Germany. The objective of the breeding program is to create new *Poinsettia* cultivars with uniform plant habit and attractive flower bract coloration.

The new *Poinsettia* originated is a naturally occurring whole plant mutation of a proprietary selection of *Euphorbia pulcherrima* Willd. identified as code number E-05-218, not patented. The cultivar Duejoker was discovered and selected by the Inventor as a flowering plant within a population of plants of the parent selection in a controlled environment in Rheinberg, Germany in January, 2002.

Asexual reproduction of the new *Poinsettia* by vegetative terminal cuttings at Rheinberg, Germany since September, 2002, has shown that the unique features of this new *Poinsettia* are stable and reproduced true to type in successive generations of asexual reproduction.

BRIEF SUMMARY OF THE INVENTION

The following traits have been repeatedly observed and are determined to be the unique characteristics of 'Duejoker'. These characteristics in combination distinguish 'Duejoker' as a new and distinct cultivar:

1. Inflorescences with red and yellow bi-colored flower bracts.
2. Dark green-colored leaves.
3. Uniform and rounded plant habit.
4. Early flowering; response time, about eight weeks.
5. Large and showy cyathia.
6. Excellent post-production longevity.

Compared to plants of the parent selection, plants of the new *Poinsettia* are larger, have darker green-colored leaves and differ in flower bract coloration.

Plants of the new *Poinsettia* can be compared to plants of the *Poinsettia* cultivar Duemirage, disclosed in a U.S. Plant patent application Ser. No. 10/859,504 filed concurrently. Plants of the new *Poinsettia* differ primarily from plants of the cultivar Duemirage in flower bract coloration.

Plants of the new *Poinsettia* can be compared to plants of the cultivar Sonora White Glitter, not patented. In side-by-side comparisons conducted in Rheinberg, Germany, plants of the new *Poinsettia* differed primarily from plants of the cultivar Sonora White Glitter in the following characteristics:

1. Plants of the new *Poinsettia* were more compact than plants of the cultivar Sonora White Glitter.
2. Plants of the new *Poinsettia* flowered later than plants of the cultivar Sonora White Glitter.
3. Plants of the new *Poinsettia* and the cultivar Sonora White Glitter differed in flower bract coloration.

BRIEF DESCRIPTION OF THE PHOTOGRAPH

The accompanying colored photograph illustrates the overall appearance of the new *Poinsettia*, showing the colors as true as it is reasonably possible to obtain in colored reproductions of this type. Colors in the photograph differ slightly from the color values cited in the detailed botanical description which accurately describe the colors of the new *Poinsettia*.

The photograph comprises a side perspective view of a single flowering plant of 'Duejoker' grown in a container.

DETAILED BOTANICAL DESCRIPTION

The new *Poinsettia* has not been observed under all possible environmental conditions. The phenotype may vary somewhat with variations in environment such as temperature, daylength and light intensity, without, however, any variance in genotype.

The aforementioned photograph, following observations and averaged measurements describe plants grown in Rheinberg, Germany during the winter under commercial practice in a glass-covered greenhouse with day and night temperatures about 22° C. and light levels about 4,500 lux. Single plants were grown in 13-cm pots and pinched once about five weeks after planting. Plants were flowered under natural season short day/long night conditions. Plants were about 16 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Duejoker.

Parentage: Naturally-occurring whole plant mutation of a proprietary selection of *Euphorbia pulcherrima* Willd. identified as code number E-05-218, not patented.

Propagation:

*Type cutting.*—Vegetative terminal cuttings.

*Time to initiate roots.*—Summer: About 9 days at 22° C. Winter: About 13 days at 22° C.

*Time to develop roots.*—Summer: About three weeks at 22° C. Winter: About four weeks at 22° C.

*Root description.*—Moderately thick, fibrous, fleshy and white in color.

*Rooting habit.*—Freely branching.

Plant description:

*Plant form.*—Inverted triangle, top of plant rounded.

*Growth habit.*—Upright and uniform plant habit; vigorous.

*Plant height.*—About 25.7 cm.

*Plant diameter or spread.*—About 36 cm.

*Lateral branch description.*—Quantity per plant: About five to seven lateral branches develop after pinching. Length: About 19.3 cm. Diameter: About 4.6 mm. Internode length: About 8 to 12 mm. Color: 137A.

*Foliage description.*—Arrangement: Alternate, single. Length: About 8.2 cm. Width: About 5.6 cm. Shape: Mostly ovate with irregular lobing. Apex: Apiculate. Base: Obtuse. Margin: Entire with irregular lobing. Venation pattern: Pinnate. Texture, upper and lower surfaces: Glabrous, smooth. Surface: Mostly flat. Color: Developing foliage, upper surface: 139A. Developing foliage, lower surface: 137B to 137C. Fully expanded foliage, upper surface: 139A. Fully expanded foliage, lower surface: 137B. Venation, upper surface: 146A to 146B. Venation, lower surface: 146B to 146C. Petiole: Length: About 4.1 cm. Diameter: About 2.4 mm. Texture, upper and lower surfaces: Glabrous, smooth. Color, upper and lower surfaces: 183A to 183B.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Response time, about eight weeks.

*Post-production longevity.*—Plants of the new *Poinsettia* maintain good substance and bract color for about eight weeks under interior conditions and about twelve weeks under greenhouse conditions.

*Quantity of inflorescences per plant.*—One per lateral branch, about five to seven.

*Inflorescence size.*—Diameter: About 21 cm. Height (depth): About 3 cm.

*Flower bracts.*—Quantity of flower bracts per inflorescence: About 15. Length, largest bracts: About 10.2 cm. Width, largest bracts: About 5.5 cm. Shape: Mostly ovate with irregular lobing. Apex: Apiculate. Base: Obtuse. Margin: Entire with irregular lobing. Texture, upper and lower surfaces: Glabrous, velvety. Surface: Mostly flat, slightly rugose. Orientation: Mostly horizontal. Color: Developing bracts, upper surface: Red, 45A, with yellow, 1C, irregular and random sectors, splashes and speckles. Developing bracts, lower surface: Red, 45A, with yellow, 1C to 1D, irregular and random sectors, splashes and speckles. Fully developed bracts, upper surface: Red, 45A to 45B, with yellow, 1B to 1C, irregular and random sectors, splashes and speckles; colors becoming closer to 45D and 1C to 1D with development. Fully developed bracts, lower surface: Red, 45D, with yellow, 1B to 1C, irregular and random sectors, splashes and speckles. Venation, upper and lower surfaces: Similar to lamina. Flower bract petiole: Length: About 3.2 cm. Diameter: About 2.4 mm. Texture, upper and lower surfaces: Glabrous, smooth. Color, upper and lower surfaces: 185A.

*Cyathia.*—Quantity of cyathia per corymb: About 15. Diameter of cyathia cluster: About 3.5 cm. Length: About 5.8 mm. Diameter: About 4.8 mm. Shape: Ovoid. Color, immature and mature: 143B. Peduncle: Length: About 4 mm. Diameter: About 2 mm. Strength/aspect: Strong, curved. Color: 143A to 143B. Stamens: Quantity of stamens per cyathium: About 35. Anther shape: Oval. Anther length: About 0.5 mm. Anther color: 187A and 9B. Amount of pollen: Moderate. Pollen color: 14A and 9B. Pistils: Quantity of pistils per cyathium: One. Pistil length: About 6 mm. Style length: About 1.4 mm. Style color: About 144B to 144C. Stigma color: 59A and 143B. Ovary color: 144A. Nectaries: Quantity of nectaries per cyathium: One. Length: About 4 mm. Color: 15A.

Disease/pest resistance: Resistance to pathogens and pests common to *Poinsettias* has not been observed on plants grown under commercial conditions.

Temperature tolerance: Plants of the new *Poinsettia* have been observed to tolerate temperatures from 12 to 40° C.

It is claimed:

1. A new and distinct cultivar of *Poinsettia* plant named 'Duejoker', as illustrated and described.

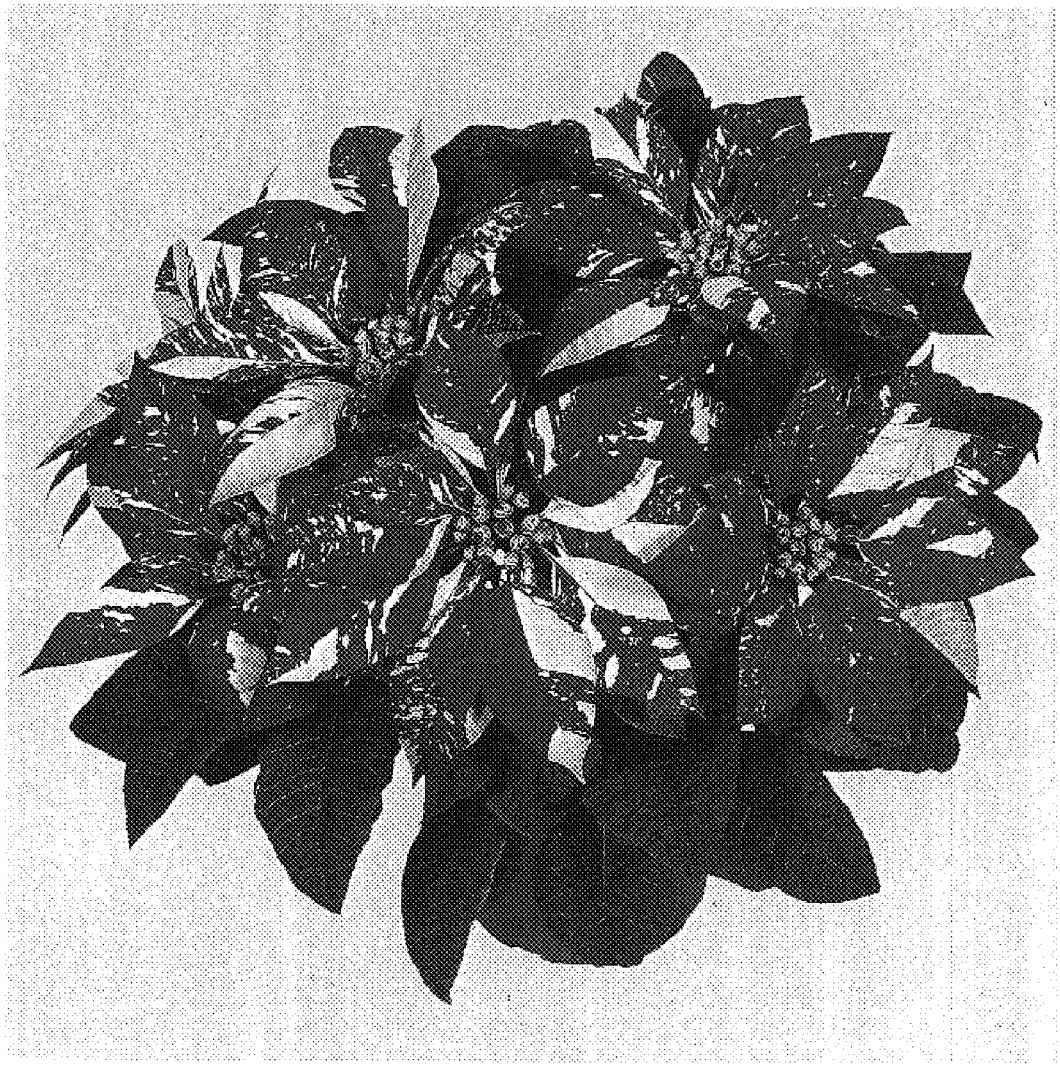

* * * * *